(12) United States Patent
Latour, Jr.

(10) Patent No.: US 6,440,060 B1
(45) Date of Patent: Aug. 27, 2002

(54) INTRA-URETHRAL DEVICE FOR INCONTINENCE AND METHOD FOR MAKING AND USING THE SAME

(75) Inventor: Robert A. Latour, Jr., Clemson, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 09/520,432

(22) Filed: Mar. 8, 2000

(51) Int. Cl.[7] .................................................. A61F 2/00
(52) U.S. Cl. ................................ 600/30; 128/DIG. 25
(58) Field of Search ............... 600/29–31; 128/DIG. 25

(56) References Cited

U.S. PATENT DOCUMENTS

| | | |
|---|---|---|
| 5,004,454 A | 4/1991 | Beyar et al. |
| 5,082,006 A | 1/1992 | Jonasson |
| 5,090,424 A | 2/1992 | Simon et al. |
| 5,114,398 A | 5/1992 | Trick et al. |
| 5,131,906 A | 7/1992 | Chen |
| 5,140,999 A | 8/1992 | Ardito |
| 5,306,226 A | 4/1994 | Salama |
| 5,476,434 A | * 12/1995 | Kalb et al. ..................... 600/30 |
| 5,724,994 A | * 3/1998 | Simon et al. ......... 128/DIG. 25 |
| 5,813,974 A | * 9/1998 | Guardia ....................... 600/30 |
| 5,954,869 A | 9/1999 | Elfersy et al. |
| 5,959,014 A | 9/1999 | Liebeskind et al. |
| 6,142,928 A | * 11/2000 | Zunker et al. ................. 600/29 |

OTHER PUBLICATIONS

Thesis entitled "Design Of An Intra–Urethral Device For Incontinence" prepared by Elizabeth M. Burke (Dec., 1996).

* cited by examiner

*Primary Examiner*—John P. Lacyk
(74) *Attorney, Agent, or Firm*—J.M. Robertson Intellectual Property, L.L.C.

(57) ABSTRACT

An intra-urethral device that can be used to inhibit leakage of urine due to incontinence is provided. The intra-urethral device can include a urethral plug made from a biocompatible, flexible material, and can be formed into an oblong shape so as to better correspond to the contours of the female urinary tract. In some instances, the intra-urethral device can also include an insertion element that can facilitate self-insertion and the ability of a fluid seal to form between the urethral plug and the walls of the urethra. Furthermore, in some instances, various mechanisms can be provided to keep the intra-urethral device substantially sterile throughout the insertion process.

40 Claims, 6 Drawing Sheets

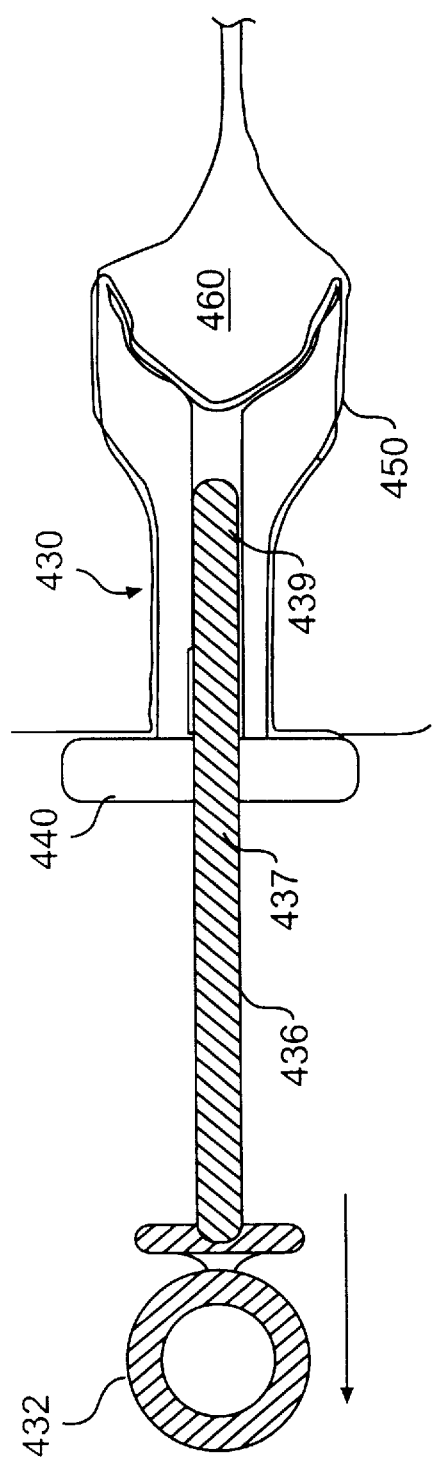
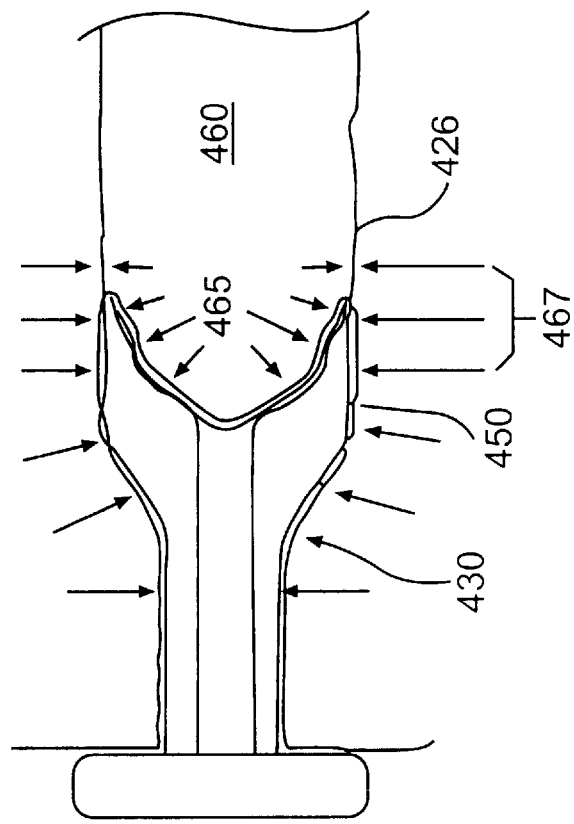
FIG. 2C
FIG. 2D

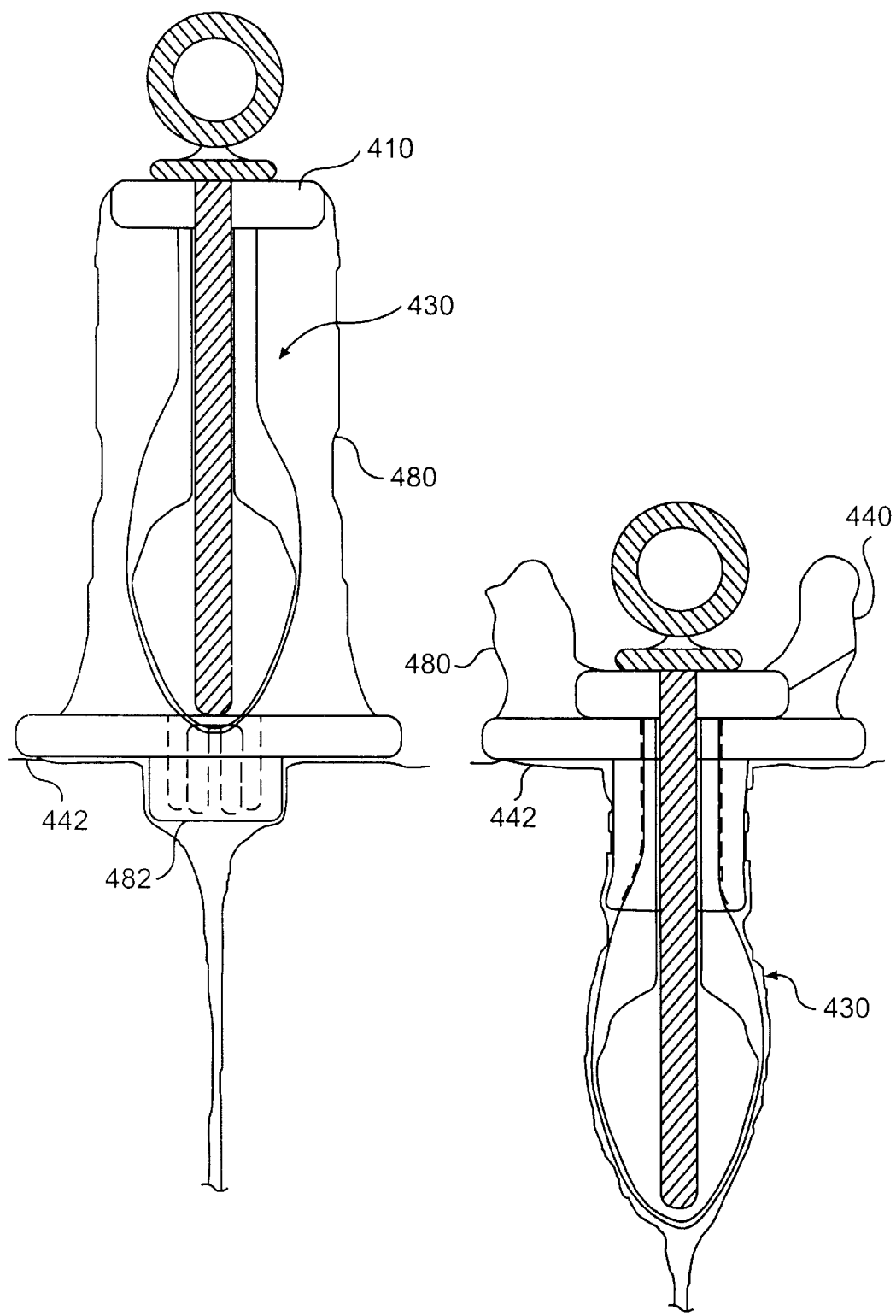
*FIG. 5A*  *FIG. 5B*

INTRA-URETHRAL DEVICE FOR INCONTINENCE AND METHOD FOR MAKING AND USING THE SAME

FIELD OF THE INVENTION

The present invention is generally directed to an intra-urethral device and method for making and using the same. More particularly, the present invention is directed to an intra-urethral device that can be used to inhibit leakage of urine due to incontinence. A device of the present invention can have a shape corresponding to the urethral orifice and also include an insertion element to facilitate self-insertion.

BACKGROUND OF THE INVENTION

Urinary incontinence is the inability of a person to control urine flow. Incontinence may result for a variety of reasons, such as anatomical abnormalities and neurological disorders. Nerve injury, childbirth, and a congenitally short urethra are all common causes of incontinence in woman. Bladder control problems are also a common cause of incontinence and affect twice as many women as men. Loss of bladder control is not a natural part of aging, although its frequency increases with aging, thus limiting the activity of many older persons.

The female urinary system is composed of two kidneys, two ureters, one bladder and one urethra. The urinary tract begins at the kidneys, continues through the ureters to the bladder, and from the bladder to the urethra, through which urine exits the body. The kidney filters the blood to remove waste and produces urine. The ureters, approximately 30 cm in length, extend from the base of the kidneys and pass through the bladder wall into the bladder itself. The bladder is a hollow muscular organ with a volume capacity of approximately 350–450 ml in a normal adult. Continence is maintained during the filling phase because urethral pressure remains greater than intravesical (bladder) pressure. When the bladder's capacity is reached, the musculature of the bladder contracts, pushing the urine through an opening in the base of the bladder to the urethra (Chisholm and Fair, Scientific Foundations of Urology, Oxford: Heinemann Medical Books, pp. 272–285, 1990).

The urethra in females is approximately 3–4 cm long and has an average inner diameter of 8 mm, varying in diameter from 4–10 mm throughout its length. A cross section of the average urethra would show that the innermost layer of the urethra hangs in folds during rest. When urine flow occurs, the urethra widens and shortens, pulling the folds back into a circular cross section. The urethra constitutes an inner, mucous-producing epithelial lining (urothelium) surrounded by a longitudinal layer of smooth muscle, which in turn is surrounded by a heavy layer of circular smooth muscle fibers. These circular smooth muscles constitute the true involuntary urethral sphincter. External to this are circular striated (voluntary) C-shaped muscles, which surround the middle third of the urethra and comprise the voluntary sphincter known as the rhabdosphincter. The pelvic floor musculature acts as a sling to keep pelvic organs in place and functioning properly.

The urinary system works to ensure that a person can control micturition. As the bladder fills, muscles stretch and nerves signal the brain that the bladder is full, leading to the urge to urinate. In continent persons, a voluntary decision is then made whether or not to urinate. When it is desirable to not urinate, the spinal cord transmits the message from the brain telling the external sphincter to contract. As the external sphincter contracts, it signals the bladder to relax and the bladder neck to stay closed, and the urge to urinate subsides. Additionally, the contraction of the sphincter increases the intraurethral pressure, such that it is greater than the intravesical pressure, thereby preventing urine passage through the urethra. This difference between the intravesical pressure and the intra-urethral pressure is termed the urethral closure pressure. When a person desires to void, the brain signals the external sphincter to relax, decreasing pressure in the urethra until urethral pressure is less than the intravesical (bladder) pressure and flow ensues.

Incontinence, or the inability to retain urine, can be broadly divided into five types. Stress incontinence results from an increase in intra-abdominal pressure, which is translated to the bladder, and for which the rhabdosphincter and pelvic floor muscles cannot compensate. Urge incontinence is a sudden need to urinate that is so urgent it cannot be controlled. This may be associated with spasm of the bladder muscle. Mixed incontinence patients experience both stress and urge incontinence. Overflow incontinence occurs when the bladder fails to empty completely due to obstruction. Small amounts of urine are lost because the bladder neck cannot remain closed against the full bladder. The last type of incontinence, functional incontinence, results when mobility limitations prevent the patient from getting to the bathroom; this is often compounded by spinal and/or nerve injury.

The present invention is designed to prevent the leakage of urine caused by incontinence, which may result from an increase in intra-abdominal pressure due to activities such as coughing, laughing, sneezing and exercising or, alternatively, can be caused by weakened pelvic floor muscles, a weakened external sphincter, a urethra which has lost muscle tone, or an abnormally short urethra.

There are currently many prosthetic devices available to compensate for incontinence. Many of the devices, however, cause urinary tract infections. Some tend to slip or migrate during use and end up in the bladder, where they may cause a great deal of harm and require invasive surgical procedures for removal. Other devices are permanent devices, which require surgery for implementation and have long term biocompatibility problems.

For instance, U.S. Pat. No. 5,131,906 to Chen discloses a device including a centrally disposed rod or tube member, a truncated spherical shell depending from one end of the member, and a plurality of elastic bands uniformly spaced around the shell periphery. Moreover, U.S. Pat. No. 5,090,424 to Simon et al. discloses a flexible urethral plug including a soft inflatable plastic catheter and a transportable fluid which is moved from an external bellows to inflate the catheter within the urethra to block urine flow. Another example of such a device is disclosed in U.S. Pat. No. 5,306,226 to Salama. Salama relates to a urine tube extending through a balloon which is inflated in the neck of the bladder to seal the urethra.

However, in contrast to the present invention, all of the above devices suffer from common disadvantages, including a susceptibility to urine encrustation and provision for direct entry of bacteria into the bladder. Additionally, the spherical design of the aforementioned devices may not totally prevent urine leakage. Because of the fluid mechanics inherent with the spherical design, back pressure caused by urine in the bladder may compress a spherical device, while simultaneously causing the urethral walls to expand, allowing urine to leak.

Other prior art incontinence control devices include devices permanently installed within the urethra, such as those disclosed in U.S. Pat. No. 5,114,398 to Trick et al.; U.S. Pat. No. 5,004,454 to Bevar et al.; and U.S. Pat. No. 5,140,999 to Ardito. However, these devices also suffer from some significant disadvantages including the requirement for surgical implantation, inclusion of metal parts subject to corrosion by urine, and need for patient manipulation to permit urination, which may introduce bacteria into the urethra.

Furthermore, temporary incontinence plugs have been previously described by U.S. Pat. No. 5,082,006 to Jonasson and by Nielson et al., "The Urethral Plug: A New Treatment Modality for Genuine Urinary Stress Incontinence in Women," *Journal of Urology* 144: 1199-1202 (1990). The Jonasson device comprises an oblong shaft having at least one knob arranged at a distance from the proximal end of the shaft. This device permits undesirable leakage, however, of approximately 15 ml of fluid. Additionally, the device also allows bacteria to enter the urethra. The device disclosed by Nielson et al. comprises a tubular shaft having at least one 7 mm sphere located along the shaft. This device has, however, been shown to slip during use, allowing the device to migrate into the bladder and requiring surgical removal. Additionally, this device has no sealing mechanism to prevent urine outflow.

In response to the need for a sealing mechanism, a urethral plug, as described in a Master's thesis entitled "Design of an Intra-Urethral Device for Incontinence," by Elizabeth M. Burke (Clemson University Department of Bioengineering, December 1996), was developed to better inhibit urine leakage. In particular, as shown in FIG. 1, a plug 10 can be positioned in urethra 22, such that the open end of plug 10 faces bladder lumen 23, allowing urine to enter the hollow cavity of plug 10. The pressure exerted by urine within the hollow cavity against the plug's sidewalls causes the sidewalls to outwardly flex in a radial direction and form a seal at urethral wall 25. An extractor element 70 can then be used to remove plug 10 from the urethra when desired.

Nevertheless, while these devices have attempted to address the problem of incontinence, none have been totally successful. In particular, the devices above do not sufficiently inhibit urine leakage and are not typically easily insertable into a urethra in a sterile manner. In view of the disadvantages associated with current treatments for incontinence, a need currently exists for a temporary device to control incontinence that is biocompatible and easily insertable by the patient in a sterile manner. A need also exists for a temporary device to control incontinence that can form a seal between the device and the intra-urethral wall to substantially inhibit urine leakage and that will not move or slip during use.

SUMMARY OF THE INVENTION

The present invention recognizes and addresses the foregoing disadvantages, and others of prior art constructions and methods.

Accordingly, it is an object of the present invention to provide an intra-urethral device for use in substantially inhibiting urinary leakage due to incontinence in women.

It is another object of the present invention to provide a flexible urethral plug for use in substantially reducing urinary leakage due to incontinence.

Yet another object of the present invention is to provide a device that can be used in conjunction with a urethral plug to facilitate the insertion of the plug from a urethra.

Still another object of the present invention is to provide a mechanism for enhancing the sterility of the urethral plug during the insertion process.

These and other objects of the present invention are achieved by providing a urethral plug that can be inserted into a urethra to substantially inhibit urinary leakage. The urethral plug can provide a resistance to the surrounding muscles as they contract, thus potentially enabling the muscles to strengthen. However, the urethral plug generally does not slip or migrate during use. A plug of the present invention can also be designed to release easily at certain pressures, or when manually removed, by engaging an elongated flexible extractor element.

In general, a urethral plug of the present invention can include a body configured to be insertable into the female urethra to form a substantial blockage against urine flow. For instance, in one embodiment, the urethral plug can have an oblong-shaped structure so as to better conform to the contours of the urethral cavity. The urethral plug can generally be made from any of a variety of materials. Typically, the urethral plug is made from a biocompatible material that may also be elastomeric, if desired. Examples of suitable materials include, but are not limited to, polyurethane, silicone, natural rubber, polyester, chloroprene, polybutadiene, etc.

In one embodiment of the present invention, the urethral plug can also be provided with various mechanisms to facilitate self-insertion of the plug from the urethra. For example, in one embodiment, the urethral plug can be used in conjunction with an insertion element, such as a shaft. In general, the insertion element can comprise a variety of materials, such as polyolefins (e.g. polypropylene), polyamides, semi-rigid rubber materials (e.g. polyurethane).

As stated, to facilitate the insertion of the urethral plug into a urethra, the insertion element can be used in conjunction with the urethral plug. For instance, in one embodiment, the urethral plug can define an opening having a closed distal end and an open proximal end such that the urethral plug can be positioned within the urethra. The shaft can be placed within the opening such that the insertion element and plug can be positioned within a urethra by utilizing the insertion element as a guide. After inserting the urethral plug, the insertion element can then be removed. For example, in one embodiment, the user can hold the urethral plug against the outer wall of the urethra while simultaneously pulling the insertion element in an outwardly direction.

In general, the withdrawal of the insertion element from the urethral can also aid in inhibiting urinal leakage. In particular, as the insertion element is withdrawn from the urethral plug, a vacuum can be created within the tip of the plug such that the tip becomes deformed. For example, the collapsible tip can deform such that the tip is inverted into a cup shape having a concave surface. In one embodiment, this concave surface can face the bladder so that a seal between the concave surface and bladder can effectively form due to fluid and rhabdosphincter pressures. It has been discovered that this seal can effectively inhibit urinal leakage.

Besides withdrawal of the insertion element, other mechanisms can be utilized to ensure that the tip of the plug becomes inverted or deformed so as to form a seal with the urethral wall. For example, in one embodiment, the insertion element can include a hollow center and an opening that is positioned near the end of the element first inserted into the urethral canal. Upon withdrawal, a vacuum pressure that is large enough to completely deform the tip is not typically created. However, the tip will become completely deformed upon application of the slightest amount of pressure, such as the pressure exerted by the flow of urine. Thereafter, upon complete deformation, a seal can be formed with the urethral wall.

Moreover, a variety of mechanisms can also be provided to allow the urethral plug to remain substantially sterile prior to and during insertion. For instance, in one embodiment, an enclosure can be provided as a cover for at least a portion of the urethral plug. Thus, as the plug is inserted through the urethra, the enclosure can collapse around the outer end of the plug. In another embodiment, a roll-out device can also be provided to enhance the ability of the plug to remain sterile during insertion into the urethra. Typically, the roll-out device includes a rolled position and an unrolled position. For example, while in the rolled-position, the roll-out device can be attached to one end of the urethral plug and inserted into the urethra. During insertion, the roll-out device can transform into the unrolled position, in which previously rolled-up material can become unraveled and substantially cover the entrance area of the urethra. Accordingly, the plug does not generally come into contact with any non-sterile surface during insertion, and thus, does not drag substantial amounts of bacteria, fungi, or other pathogenic microorganisms into the urethra.

Other objects, features and aspects of the present invention are discussed in greater detail below.

BRIEF DESCRIPTION OF THE DRAWINGS

FIG. 2 illustrates one embodiment of the present invention, in which FIG. 2C shows partial removal of the insertion element following intra-urethral insertion of the device, and FIG. 2D shows the device positioned in the urethra with the resulting seal formed between the urethral wall and the sidewall of the device.

FIG. 5 is another embodiment of the device depicted in FIG. 2, in which FIG. 5A shows the device prior to intra-urethral insertion and FIG. 5B shows the device during insertion.

DETAILED DESCRIPTION OF THE INVENTION

Figure 1:
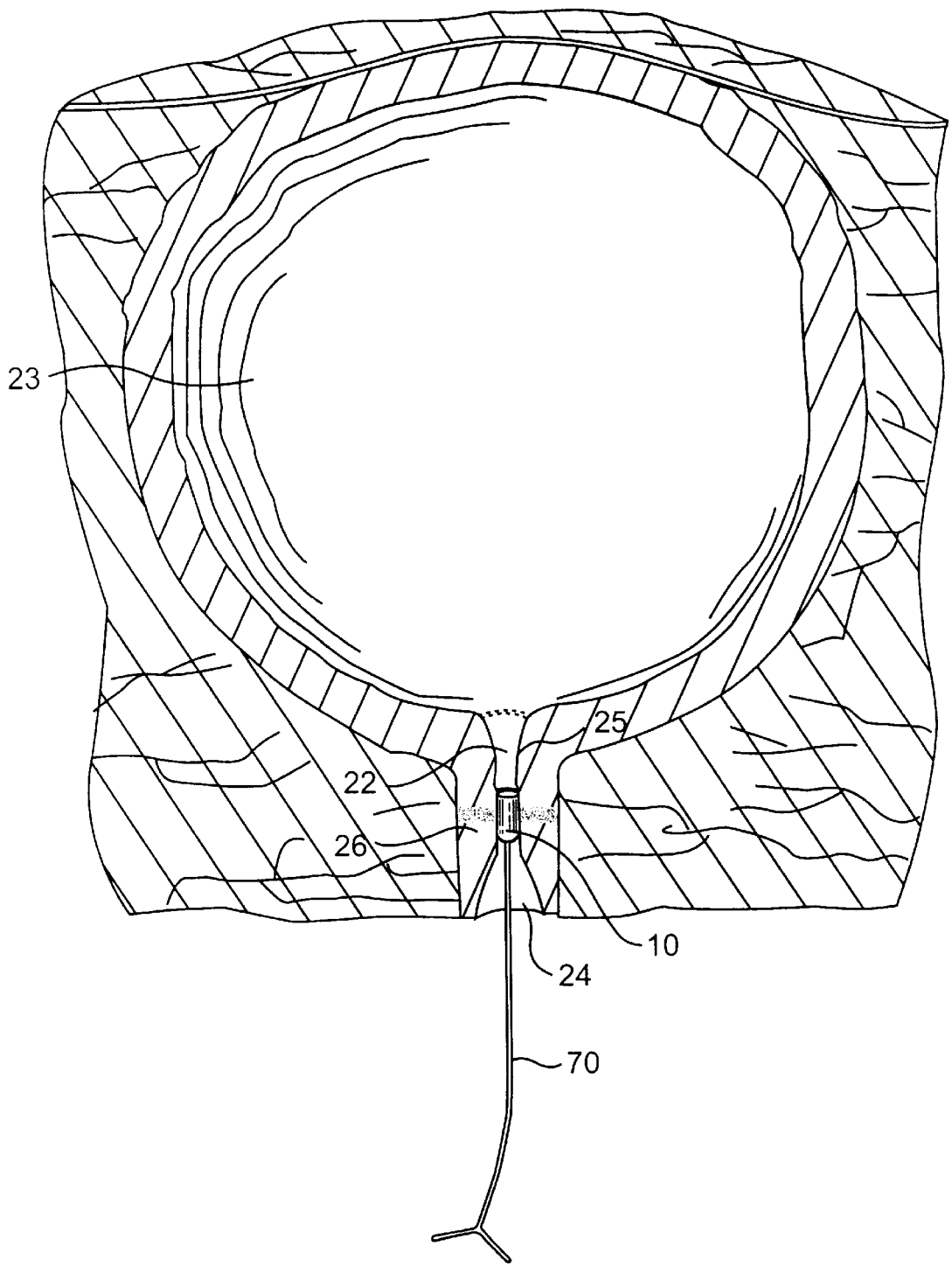
FIG. 1 is a cross-sectional view of the female urinary tract showing positioning of a prior art intra-urethral device.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description.

The present invention is generally directed to a device and method for treating urinary incontinence in women on a short-term basis. Specifically, a device of the present invention can be designed to be disposed after a single use. In this regard, a device of the present invention can include a flexible urethral plug that can be easily inserted by the patient into her urethra. For instance, one embodiment of a urethral plug of the present invention is depicted in FIGS. 2A–2D. As shown, urethral plug 430 can include a central tube body 452 and a collapsible front tip 450. Moreover, urethral plug 430 can also include an external flange 440 to substantially prevent over-insertion of the plug and to aid in the removal of plug 430.

In general, a urethral plug of the present invention can be made in a variety of ways. Typically, a urethral plug of the present invention can be made from a material that is generally biocompatible such that it is suitable for contact with the urethra. For instance, in one embodiment, biocompatible polymers can be utilized having various lengths and sizes. In some embodiments, a urethral plug of the present invention can be made from a biocompatible material that is also flexible. Some examples of suitable flexible materials can include elastomeric polymers, such as polyurethane, silicone, natural rubber, polyester, chloroprene, polybutadiene, combinations thereof, or any other elastomeric material suitable for urethral contact. One particular example of an elastomer suitable for use in making a plug of the present invention is silicone rubber, such as medical grade silicone rubber commonly used in various medical devices. However, it should be understood that any elastomeric material having sufficient flexibility to permit the device's collapsible tip to expand radially to form a seal between the device and urethra wall can be used in the present invention.

It also should be understood that a urethral plug of the present invention need not be made from the same material(s). For example, collapsible tip 450, tube 452, and external flange 440 may all contain different material(s), if desired. In one embodiment, for instance, collapsible tip 450 can be made from a flexible elastomeric material, while external flange 440 and tube 452 can conversely be made from a less flexible or non-flexible material.

Moreover, urethral plug 430 can also generally possess any desired dimension or shape in accordance with the present invention. The proper size for use is usually determined by a physician, after measuring the patient's urethra. In particular, a urethral plug 430 can be made into a variety of different shapes and sizes to better conform to different urethras. Moreover, in some embodiments, because the plug can also conform to the size and shape of the urethra after insertion, there may be no need to custom make the plug. For example, in one embodiment, as shown in FIGS. 2A–2D, urethral plug 430 can have an oblong shape corresponding to the urethral orifice.

In this regard, a urethral plug of the present invention can generally have of any length and width dimension. For example, the length dimension of plug 430 can range from about 1.5 cm to about 3.0 cm in length, in some embodiments from about 2.0 cm to about 2.6 cm, and in some embodiments, the length dimension can be about 2.4 cm. In one embodiment, for example, as shown in FIGS. 2A–2D, urethral plug 430 can have a length dimension approximately equal to the combined values of the dimensions represented as "A", "B", and "C", and have a width approximately equal to the value represented as "D". "A", "B", "C", and "D" can generally be selected to have any value, depending on the desired shape and size of the urethral plug. For example, in one embodiment, the dimensions represented as "A", "B", and "C" are each about 1.0 cm. Moreover, in another embodiment, the dimension represented as "D" is about 0.8 cm.

In addition, the thickness of the urethral plug, including tube 452 and collapsible tip 450, can vary as desired. For example, in one embodiment, urethral plug 430 can have a relatively constant thickness. In particular, the thickness can range from about 0.5 mm to about 1.5 mm, and in one embodiment, the thickness can be about 1 mm. In an alternate embodiment, urethral plug 430 can have variable thicknesses along its length. For example, tube 452 can have a thickness of about 1 mm thick adjacent flange 440, thereby tapering to a thickness of about 0.5 mm thickness at collapsible tip 450. The variable thickness of collapsible tip 450 can provide increased flexibility to facilitate expansion of the tip in a radial direction to form a seal between tip 450 and the patient's urethral wall.

In general, the size of urethral plug 430 in relation to the urethra may be such that plug 430 can inhibit urine leakage without external pressure being applied by the periurethral muscle, until urine back pressure reaches approximately 0.3–0.4 psi. At approximately 0.3–0.4 psi, plug 430 can release from its intra-urethral position and move towards the external urethral meatus. However, in some embodiments, application of as little as 0.1 psi pressure by the surrounding periurethral muscle can significantly increase the "holding power" of the urethral plug 430. When the patient voluntarily releases external pressure applied to urethral plug 430 by the periurethral muscle, the urethra can shorten and dilate, causing urethral plug 430 to be released from the urethra and facilitating urination.

According to the present invention, an insertion element, such as inner shaft 436, can, in some embodiments, be provided to facilitate the insertion of urethral plug 430. As shown, in one embodiment, inner shaft 436 can include a handle 432 and a flange 435 to prevent inner shaft 436 from slipping into plug 430.

An insertion element of the present invention can generally be made any of a variety of materials, such as rigid or semi-rigid materials. In some embodiments, for instance, the insertion element can contain plastic materials, such as polyolefins, polyamides, etc. For example, in one embodiment, the insertion element can contain polypropylene. Moreover, in another embodiment, the insertion element can contain a semi-rigid rubber material, such as polyurethane. In addition, the insertion element can also be formed to have any desired shape or size. For example, in one embodiment, the insertion element can be a shaft having at least one rounded end. An insertion element having a rounded end, in some instances, can help prevent tearing of the collapsible tip when contacted therewith during insertion.

Figure 2A:
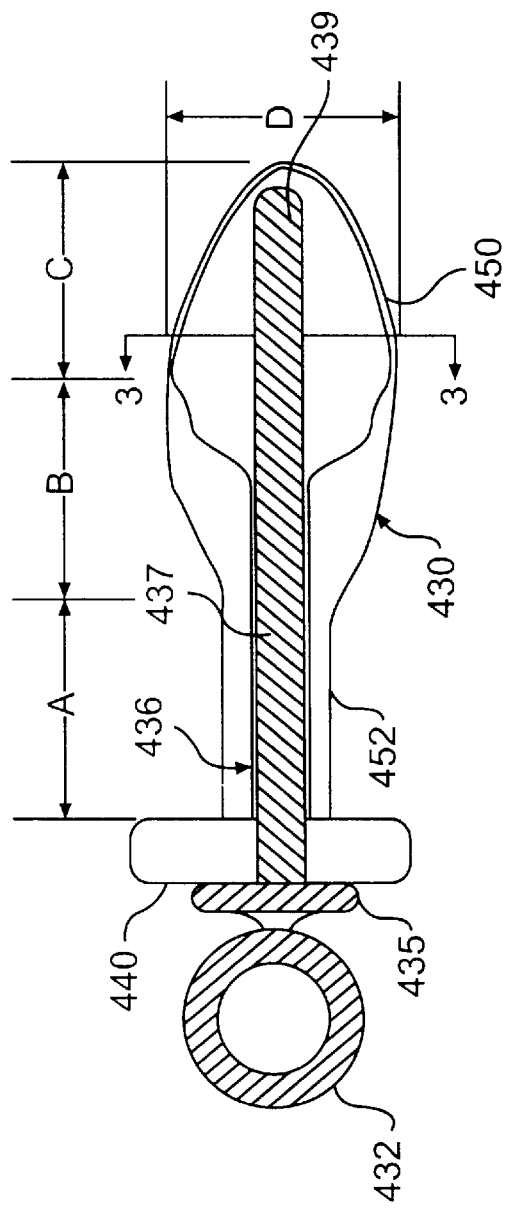
FIG. 2A shows the device prior to intra-urethral insertion.
Figure 2B:
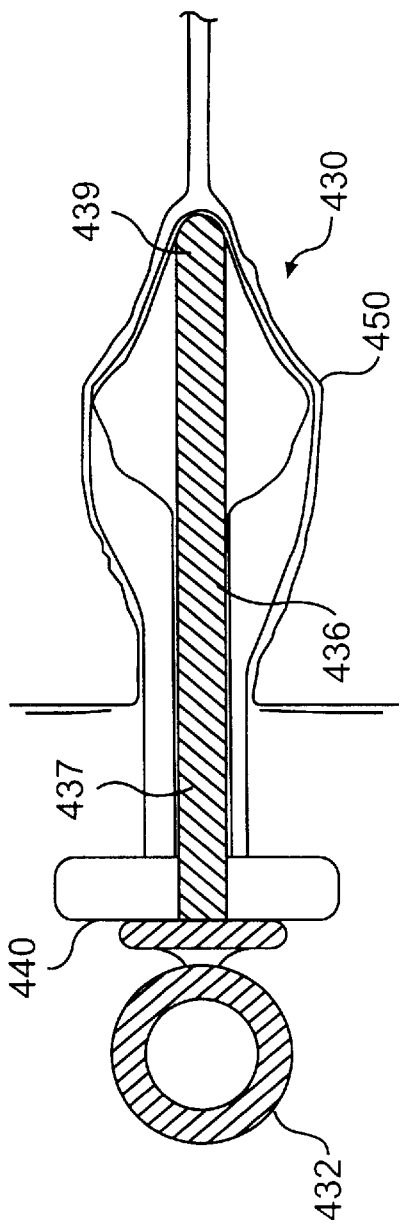
FIG. 2B shows the device during insertion.

As stated above, the insertion element can typically be utilized to facilitate the insertion of urethral plug into a urethra. For instance, as shown in FIGS. 2B–2D, a user can insert urethral plug 430 into a urethra by utilizing inner shaft 436 as a guide. In particular, by holding handle 432 in an outwardly extended position, a user can easily insert collapsible tip 450 through the urethral opening and into urethral canal 460. In this regard, it has been discovered that an insertion element of the present invention can beneficially allow a user to self-insert a urethral plug into the urethra.

After inserting the urethral plug, the insertion element can then be removed. For example, as depicted in FIG. 2C, a user can withdraw inner shaft 436 by pulling handle 432 in an outwardly direction, as indicated by the arrow depicted in FIG. 2C, while simultaneously holding external flange 440 against external urethral meatus.

According to the present invention, the outwardly movement of inner shaft 436 from urethral plug 430 during withdrawal may allow a vacuum to be created within collapsible tip 450. This vacuum can cause tip 450 to invert into a cup shape, as depicted in FIGS. 2C–2D, such that the concave surface of the cup faces the bladder. The concave surface can allow urethral plug 430 to effectively form a seal against involuntary leakage. In particular, as shown in FIG. 2D, the fluid pressure from the bladder (indicated by directional arrows 465) and the rhabdosphincter pressure (indicated by directional arrows 467), can hold collapsible tip 450 against intraurethral wall 426, thus forming a seal around plug 430 to inhibit urine leakage. If desired, the outside of the urethral plug can be also coated with a lubricant, such as VASELINE or K-Y JELLY, prior to insertion into the urethra in order to assist in seal formation and to protect sensitive urethral tissue.

In some instances, it may not be desired to create a vacuum within collapsible tip 450 upon withdrawal of inner shaft 436 from the urethra. In particular, the withdrawal of the insertion element from the urethra can, in certain circumstances, cause tissue to stretch and/or irritate the urethra walls. Such tissue stretching or irritation can be easily inhibited by allowing the collapsible tip to completely collapse or deform only in the presence of a fluid.

Figure 3:
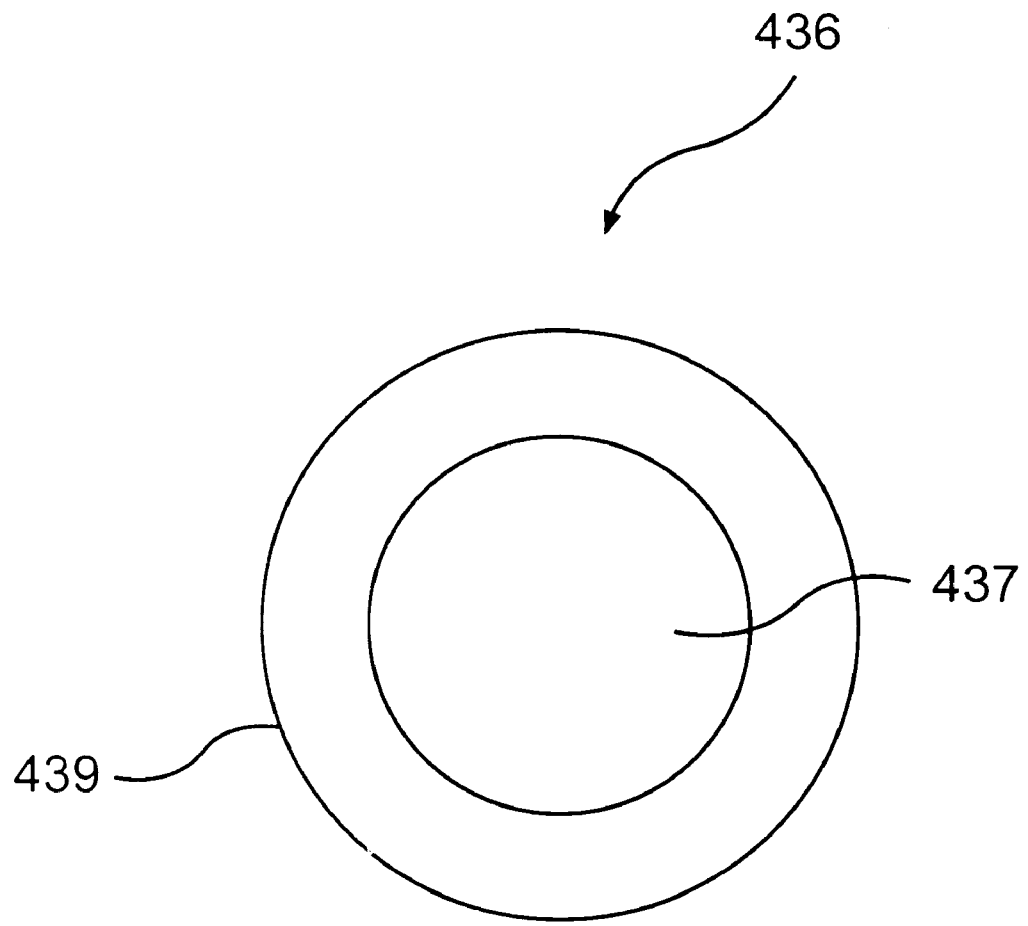
FIG. 3 is a cross-sectional view taken along a line 3—3 of another embodiment of the insertion element depicted in FIG. 2 in which the insertion element has a hollow center.
Figure 4:
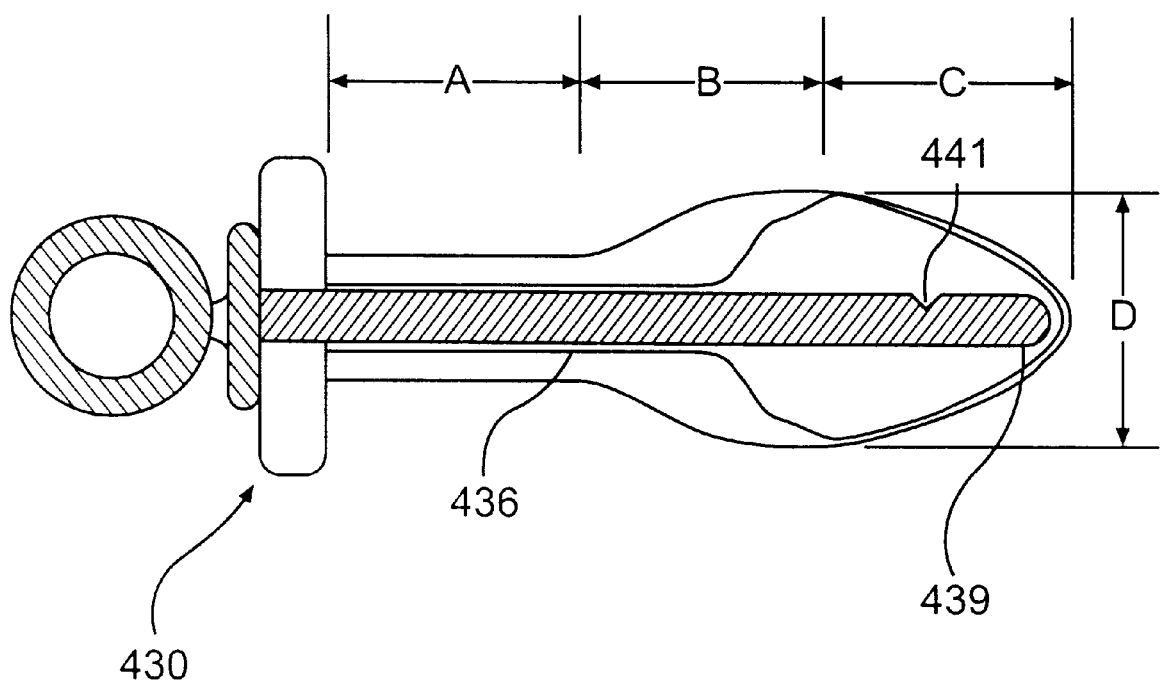
FIG. 4 is another embodiment of the device depicted in FIG. 2, in which the insertion element includes an opening.

In this regard, in some embodiments, the insertion element, such as inner shaft 436, can be provided with a center that is hollow. For instance, as shown in FIG. 3, center portion 437 can have a hollow center 437a that opens at distal end 439. Thus, due to the hollow center that opens at the end of the shaft, a vacuum pressure great enough to completely collapse tip 450 cannot be created upon withdrawal of shaft 436. Nevertheless, after withdrawal of shaft 436, collapsible tip 450 will completely deform upon the application of only a small amount of pressure. As such, such a low pressure can be provided by the flow of urine at a later point in time, which thereby causes the tip 450 to completely deform and form a seal with the urethral wall, as described above. It should be understood that the entire distal end of the insertion element need not be open to the hollow center, and that even a small hole in the distal end can substantially prevent too large of a vacuum pressure from forming. Moreover, such a small opening need not be located at the distal end of the insertion element, but can generally be positioned anywhere along the insertion element, as long as the opening is in communication with the hollow center of the insertion element. For instance, as shown in FIG. 4, a small opening 441 near the tip of distal end 439 can be used.

Furthermore, a urethral plug of the present invention can also have varying diameters. For example, the collapsible tip can be formed to possess varying degrees of deformation when the vacuum is created as described above. For example, a collapsible tip, in a fully expanded position, can generally have an outer diameter from about 4.0 mm to about 10.0 mm, in some embodiments from about 5.0 mm to about 8.0 mm, and in some embodiments, can be about 6 mm. In addition, the tube 452 can also have a variety of different diameters as well. For instance, the diameter of tube 452 can range from about 2 mm to about 8 mm, in some embodiments from about 4 mm to about 6 mm, and in some embodiments, can be about 5 mm.

In accordance with the present invention, a urethral plug of the present invention can generally be removed in a variety of ways. In most embodiments, a urethral plug of the present invention can be removed without the aid of a medical professional. In particular, removal can normally be accomplished manually or by voluntary urinary exertion. Moreover, although not necessary, a variety of other mechanisms can also be utilized to facilitate the removal of the urethral device. For instance, as shown in FIG. 1, urethral plug 430 can include an removal device, such as extractor element 70, to facilitate manual removal of the plug. Although FIG. 1 depicts a prior art device, it should be understood that the extractor element depicted therein is equally applicable to a urethral plug of the present invention. For example, in some embodiments, extractor element 70 can be an elongated flexible element, such as a string, a filament, a cord, and the like. Moreover, if desired, extractor element 70 can also be manufactured separately from urethral plug 413 and subsequently secured thereto. As shown in FIG. 1, for example, extractor element 70 can allow the patient to facilitate manual plug removal as desired, by manually exerting pressure on extractor element 70 in a downward direction. Additionally, should expulsion not occur when plug 430 is released from its intra-urethral location, extractor element 70 can also allow the patient to completely remove plug 430. It should be understood that an extractor element may be secured to a plug of the present invention by any suitable means known in the art, as long as adequate strength is present to facilitate manual removal of the plug by applying downward force to the extractor element. For example, in one embodiment, extractor element 70 may be molded as a unitary structure with urethral plug 430.

In one embodiment, a mechanism can also be utilized to allow the urethral device to be self-inserted in a sterile manner. For instance, referring to FIGS. 5A–5B, an enclosure, such as bag 480, can be provided as a cover for urethral plug 430 to prevent substantial contamination of the plug before and during insertion. In general, bag 480 can be made from any of a variety of materials, such as various plastics. As shown, bag 480 can also be sealed to urethral plug 430 via a positioning flange 442 according to any sealing method known in the art. In one embodiment, plug 430 can be inserted into the urethra by first maneuvering positioning flange 442 such that plug 430 is properly aligned with the urethra opening. As plug 430 is inserted through the urethra opening, bag 480 can collapse around the outer end of plug 430. Once collapsed, bag 480 can then be torn away, if desired, to provide a user with better access to plug 430. However, in other embodiments, it may be desired to allow bag 480 to remain around the outer end of plug 430 after it has collapsed.

In addition, in some embodiments, a roll-out device, such as roll-out nipple 482, can also be provided to enhance the ability of plug 430 to remain sterile during insertion into the urethra. Although a roll-out nipple is depicted and described herein, it should be understood that any other suitable device capable of enhancing the sterility of the urethral plug can be utilized in accordance with the present invention. In one embodiment, as stated, roll-out nipple 482 can provide enhanced sterility. In particular, the insertion of plug 430 causes roll-out nipple 482 to unravel, as shown in FIG. 5B, such that it can cover the entrance area of the urethra as plug 430 is inserted therein. As a result, plug 430 does not generally come into contact with any non-sterile surface, and thus, does not drag substantial amounts of bacteria, fungi, or other pathogenic microorganisms into the urethra, prior to or during insertion.

It has been discovered that the collapsible tip of an intra-urethral device of the present invention can allow for large variations in its girth, thus providing a measure of resistance to the surrounding urinary tract muscles. This resistance can help the urinary tract muscles at least grow stronger as they work to prevent urine flow. In some instances, this resistance can at least maintain existing muscle strength and prevent degeneration that may result from the use of rigid devices, which can inhibit sphincter control during urination.

Moreover, the collapsible tip of the intra-urethral device can also ensure that an increase in external pressure will not adversely affect the use of the device by creating gaps around the external circumference of the device and permit leakage. The intra-urethral device can compress, in response to the increase in external urethral pressure, and thereby reduce comparably in its girth. Once the seal between the device and the urethra is achieved, a change in the size of the device does not generally affect its performance because the thickness of the walls is sufficient to resist circumferential buckling action.

It should be understood that the present invention is not limited to the specific polymers or processes described herein and that any materials equivalent to those described falls within the scope of the present invention. Preparation methods of the intra-urethral device and steps for its use in inhibiting urine leakage due to incontinence are merely exemplary so as to enable one of ordinary skill in the art to produce the intra-urethral plug and use it according to the described process and its equivalents.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. An incontinent device for use in a female urinary tract comprising:
   a urethral plug defining an internal chamber, said internal chamber having a distal end and a proximal end, said distal end of said internal chamber being closed and said proximal end of said internal chamber being open, said urethral plug being configured to be positioned within a urethra;
   an insertion element adapted to be inserted into said internal chamber of said urethral plug through said open proximal end, said insertion element being further adapted to be withdrawn from said urethral plug; and
   said distal end of said urethral plug deforming after withdrawal of said insertion element from said urethral plug with said urethral plug positioned within said urethra, said deformable distal end being cooperable with the walls of said urethra to form a seal therewith for substantially inhibiting urine leakage from said urethra around said urethral plug.

2. An incontinent device as defined in claim 1, wherein said urethral plug is made from a biocompatible material.

3. An incontinent device as defined in claim 1, wherein said urethral plug is made from an elastomeric polymer.

4. An incontinent device as defined in claim 3, wherein said elastomeric polymer is a silicon rubber.

5. An incontinent device as defined in claim 1, wherein said urethral plug includes an external flange for inhibiting over-insertion of said urethral plug into said urethra.

6. An incontinent device as defined in claim 1, wherein said insertion element is an elongated structure made from a material selected from the group consisting of polyolefins, polyamides, rubber materials, and combinations thereof.

7. An incontinent device as defined in claim 6, wherein said insertion element is made from polyurethane.

8. An incontinent device as defined in claim 6, wherein said insertion element is made from polypropylene.

9. An incontinent device as defined in claim 1, wherein said deformable distal end is capable of assuming a generally concave configuration.

10. An incontinent device as defined in claim 1, further comprising a sterile enclosure, said sterile enclosure surrounding at least a portion of said urethral plug.

11. An incontinent device as defined in claim 10, wherein said sterile enclosure has a positioning flanged adhered thereto.

12. An incontinent device as defined in claim 10, further comprising a roll-out device having a rolled and unrolled position, said roll-out device being in cooperable communication with said insertion element such that the insertion of said insertion element into said urethra places said roll-out device in said unrolled position.

13. An incontinent device as defined in claim 1, wherein said insertion element defines a hollow center.

14. An incontinent device as defined in claim 13, wherein said insertion element has a distal end and a proximal end, said insertion element further defining an opening in proximity to said distal end of said insertion element.

15. An incontinent device as defined in claim 1, wherein said insertion element has a distal end and a proximal end, said distal end of said insertion element being rounded.

16. An incontinent device for use in a female urinary tract comprising:
   a urethral plug defining an internal chamber, said internal chamber having a distal end and a proximal end, said distal end of said internal chamber being closed and said proximal end of said internal chamber being open, said urethral plug being configured to be positioned within a urethra; and
   an enclosure surrounding at least a portion of said urethral plug wherein said enclosure is adapted to provide a barrier between said urethral plug and atmosphere during insertion of said urethral plug so as to substantially maintain the sterility of said urethral plug.

17. An incontinent device as defined in claim 16, further comprising a roll-out device having a rolled and unrolled position, said roll-out device being capable of being placed in said unrolled position when said urethra plug is inserted into said urethra.

18. An incontinent device as defined in claim 16, wherein said urethral plug is made from a biocompatible material.

19. An incontinent device as defined in claim 16, wherein said urethral plug is made from a elastomeric polymer.

20. An incontinent device as defined in claim 19, wherein said elastomeric polymer is a silicon rubber.

21. An incontinent device as defined in claim 16, wherein said urethral plug includes an external flange for inhibiting over-insertion of said urethral plug into said urethra.

22. An incontinent device as defined in claim 16, wherein said insertion element is an elongated structure made from a material selected from the group consisting of polyolefins, polyamides, rubber materials, and combinations thereof.

23. An incontinent device as defined in claim 22, wherein said insertion element is polyurethane.

24. An incontinent device as defined in claim 22, wherein said insertion element is polypropylene.

25. An incontinent device as defined in claim 16, wherein said sterile enclosure has a positioning flange adhered thereto.

26. An incontinent device for use in a female urinary tract comprising:
   a urethral plug defining an internal chamber, said internal chamber having a distal end and a proximal end, said distal end of said internal chamber being closed and said proximal end of said internal chamber being open, said urethral plug being configured to be positioned within a urethra;
   an insertion element adapted to be inserted into said internal chamber of said urethral plug through said open proximal end, said insertion element being further adapted to be withdrawn from said urethral plug, said insertion element having a substantially solid center; and
   said distal end of said urethral plug deforming soon after withdrawal of said insertion element from said urethral plug with said urethral plug positioned within said urethra, said deformable distal end being cooperable with the walls of said urethra to form a seal therewith for substantially inhibiting urine leakage from said urethra around said urethral plug.

27. An incontinent device as defined in claim 26, wherein said deformable distal end is capable of assuming a generally concave configuration.

28. An incontinent device as defined in claim 26, further comprising an enclosure surrounding at least a portion of said urethral plug so that said enclosure is capable of substantially maintaining the sterility of said urethral plug.

29. An incontinent device as defined in claim 26, further comprising a roll-out device having a rolled and unrolled position, said roll-out device being in cooperable communication with said insertion element such that the insertion of said insertion element into said urethra places said roll-out device in said unrolled position.

30. An incontinent device for use in a female urinary tract comprising:
   a urethral plug defining an internal chamber, said internal chamber having a distal end and a proximal end, said distal end of said internal chamber being closed and said proximal end of said internal chamber being open, said urethral plug being configured to be positioned within a urethra;
   an insertion element adapted to be inserted into said internal chamber of said urethral plug through said open proximal end, said insertion element being further adapted to be withdrawn from said urethral plug, said insertion element having a distal end and a proximal end, said insertion element defining a hollow center and an opening in proximity to said distal end, said opening being in communication with said hollow center; and
   said distal end of said urethral plug being capable of substantially deforming only upon receipt of a fluid after withdrawal of said insertion element from said urethral plug with said urethral plug positioned within said urethra, said deformable distal end being cooperable with the walls of said urethra to form a seal therewith, said seal substantially inhibiting urine leakage from said urethra around said urethral plug.

31. An incontinent device as defined in claim 30, wherein said deformable distal end is capable of assuming a generally concave configuration.

32. An incontinent device as defined in claim 30, further comprising an enclosure surrounding at least a portion of said urethral plug so that said enclosure is capable of substantially maintaining the sterility of said urethral plug.

33. An incontinent device as defined in claim 30, further comprising a roll-out device having a rolled and unrolled position, said roll-out device being in cooperable communication with said insertion element such that the insertion of said insertion element into said urethra places said roll-out device in said unrolled position.

34. An incontinent device as defined in claim 30, wherein said fluid is urine.

35. A method of substantially inhibiting the leakage of urine from a female urinary tract, said method comprising the steps of:

provising a urethral plug, said urethral plug defining an internal chamber, said internal chamber having a distal end and a proximal end, said distal end of said internal chamber being closed and said proximal end of said internal chamber being open;

placing an insertion element into said internal chamber of said urethral plug through said proximal end;

inserting said urethral plug and said insertion element into a urethra; and withdrawing said insertion element from said urethral plug with said urethral plug remaining substantially within said urethra, said withdrawal of said insertion element causing said distal end to at least slightly deform, said distal end being cooperable with the walls of said urethra to form a seal therewith for substantially inhibiting urine leakage from said urethra around said urethral plug.

36. A method as defined in claim 35, wherein said distal end deforms to form said seal only upon receipt of a fluid after the step of withdrawing said insertion element.

37. A method as defined in claim 36, wherein said fluid is urine.

38. A method as defined in claim 35, wherein said distal end is capable of assuming a generally concave configuration.

39. A method as defined in claim 35, further comprising the step of enclosing at least a portion of said urethral plug with an enclosure so that said enclosure is capable of substantially maintaining the sterility of said urethral plug.

40. A method as defined in claim 35, further comprising the step of providing a roll-out device having a rolled and unrolled position, wherein the insertion of said insertion element and said urethra plug into said urethra places said roll-out device in said unrolled position.

* * * * *